United States Patent [19]

Kajioka et al.

[11] 4,318,731
[45] Mar. 9, 1982

[54] DELTA-2-1,2,4-TRIAZOLIN-5-ONE DERIVATIVES AND HERBICIDAL USAGE THEREOF

[75] Inventors: Mitsuru Kajioka, Sakai; Hitoshi Kurono, Toyonaka; Katsumasa Okawa, Kawachinagano; Tatsuo Harada, Mitaka, all of Japan

[73] Assignee: Nihon Nohyaku Co., Ltd., Japan

[21] Appl. No.: 162,558

[22] Filed: Jun. 24, 1980

[30] Foreign Application Priority Data

Aug. 25, 1979 [JP] Japan ................................ 54/108509
Apr. 22, 1980 [JP] Japan ................................ 55/53206

[51] Int. Cl.³ .................... A01N 43/64; C07D 249/12
[52] U.S. Cl. ......................................... 71/92; 548/263; 548/265; 560/29; 560/30; 564/310
[58] Field of Search ..................... 548/263, 265; 71/92

[56] References Cited

U.S. PATENT DOCUMENTS 3,290,327 12/1966 Palazzo ................................ 548/263
3,514,466 5/1970 Stahle et al. ........................ 548/263

FOREIGN PATENT DOCUMENTS 2725148 12/1978 Fed. Rep. of Germany ...... 548/262
54-3071 1/1979 Japan ................................... 548/263
1068083 5/1967 United Kingdom ................ 548/263

Primary Examiner—Alton D. Rollins
Attorney, Agent, or Firm—Karl W. Flocks

[57] ABSTRACT

A novel $\Delta^2$-1,2,4-traizolin-5-one derivative having a herbicidal activity, which is represented by the formula

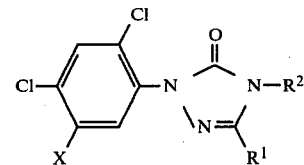

wherein, $R^1$ is a $C_1$–$C_4$ alkyl; $R^2$ is a hydrogen atom, a $C_1$–$C_6$ alkyl group, or a $C_2$–$C_4$ alkenyl group; and X is a hydroxy group, a $C_1$–$C_4$ alkyl group, a $C_1$–$C_6$ alkyloxy group, an alkyloxyalkyloxy group of which two alkyls may be same as or different from each other and each alkyl is of $C_1$–$C_4$, a $C_2$–$C_4$ alkenyloxxy, or an alkyloxycarbonylalkyloxy group of which two alkyls may be same as or different from each other and each alkyl is of $C_1$–$C_4$.

12 Claims, No Drawings

Δ²-1,2,4-TRIAZOLIN-5-ONE DERIVATIVES AND HERBICIDAL USAGE THEREOF

The present invention relates to Δ²-1,2,4-triazoline-5-one derivatives and usage thereof, which are represented by the formula (I)

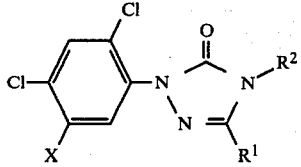

wherein, $R^1$ is a $C_1$–$C_4$ alkyl; $R^2$ is a hydrogen atom, a $C_1$–$C_6$ alkyl group or a $C_2$–$C_4$ alkenyl group and X is a hydroxy group, a $C_1$–$C_4$ alkyl group, a $C_1$–$C_6$ alkyloxy group, an alkyloxyalkyloxy group of which two alkyls may be same as or different from each other and each alkyl is of $C_1$–$C_4$, a $C_2$–$C_4$ alkenyloxy, or an alkyloxycarbonylalkyloxy group of which two alkyls may be same as or different from each other and each alkyl is of $C_1$–$C_4$.

In the above formula (I), the $C_1$–$C_4$ alkyl group of $R^1$ or of X, the same group in the alkyloxyalkyloxy of X, and the same group in the alkyloxycarbonyl alkyloxy of X include, for example, methyl, ethyl, n-propyl, i-propyl, n-butyl, iso-butyl, sec-butyl, and tert.-butyl groups.

The $C_1$–$C_6$ alkyl group of $R^2$ and the same group in the alkyloxy of X include, for example, methyl, ethyl, n-propyl, iso-propyl, n-butyl, iso-butyl, sec-butyl, tert-butyl, n-pentyl and n-hexyl groups;

The $C_2$–$C_4$ alkenyl group of $R^2$ and the same group in the alkenyloxy of X include, for example, 3-butenyl, 2-butenyl, 2-methylallyl and allyl groups.

The compounds represented by the above formula (I) are especially useful as herbicides (including algicides; the same applies hereinafter).

These are novel compounds unreported in the literlature. As examples of typical processes for synthesis thereof, the following processes A, B, and C are given. The reaction paths are schematically shown below:

Process A:

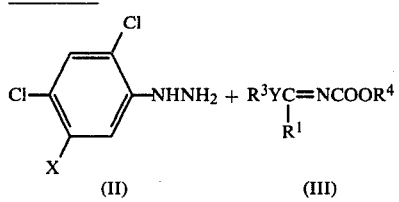

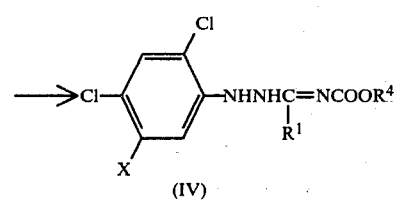

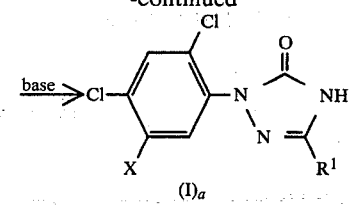

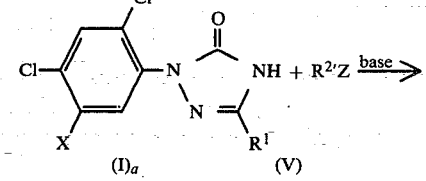

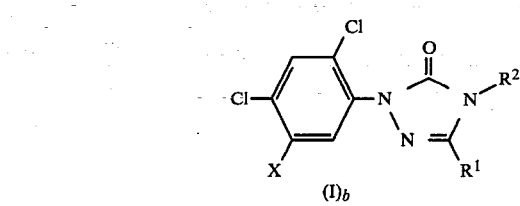

wherein, $R^1$ and X are the same as defined above, $R^{2'}$ is a $C_1$–$C_6$ alkyl or a $C_2$–$C_4$ alkenyl, $R^3$ and $R^4$ may be the same or different and are each methyl or ethyl, Y is an oxygen or sulfur atom, and Z is a halogen atom.

Thus, one of the compounds of formula (I), a compound of (I)$_a$, can be obtained by reacting a compound of (II) with a compound of (III) in an inert solvent, and subjecting the resulting compound of (IV) with or without isolation to ring closure in the presence of a base. Further, a compound of (I)$_b$, one of the compounds represented by formula (I), can be obtained by reacting the compound of (I)$_a$ with a compound of (V) in the presence of a base.

As the inert solvent used, any solvent not seriously disturbing this type of reaction may be used; for example it is possible to use aromatic hydrocarbons such as benzene, toluene, and xylene; ethers such as ethyl ether, tetrahydrofuran, and dioxane; alcohols such as methanol, ethanol, propanol, and ethyleneglycol; ketones such as acetone, methyl ethyl ketone, and cyclohexanone; lower fatty acid esters such as ethyl acetate; lower fatty acid amides such as dimethylformamide and dimethylacetamide; water; and dimethylsulfoxide. These solvents may be used each alone or in combination with one another.

The bases which can be used for the above reaction include inorganic bases such as, for example, sodium carbonate, potassium carbonate, sodium hydrogencarbonate, potassium hydrogencarbonate, caustic soda, caustic potash, and alkali metal alcoholates; and organic bases such as, for example, pyridine, trimethylamine, triethylamine, diethylaniline, and 1,8-diazabicyclo-[5,4,0]-7-undecene.

In case of reacting a compound of (V) with a compound of (I)$_a$ a two-phase reaction can also be applied between an aqueous solution layer containing a base such as caustic soda and an organic solvent layer in the presence of a phase transfer catalyst such as triethylbenzylammonium chloride, whereby compounds of formula (I)$_b$ can be synthesized in good yields.

A compound of (III) can be obtained, for example, by way of the reactions represented by the following equations:

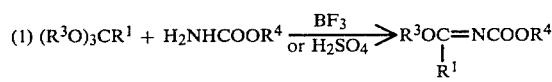

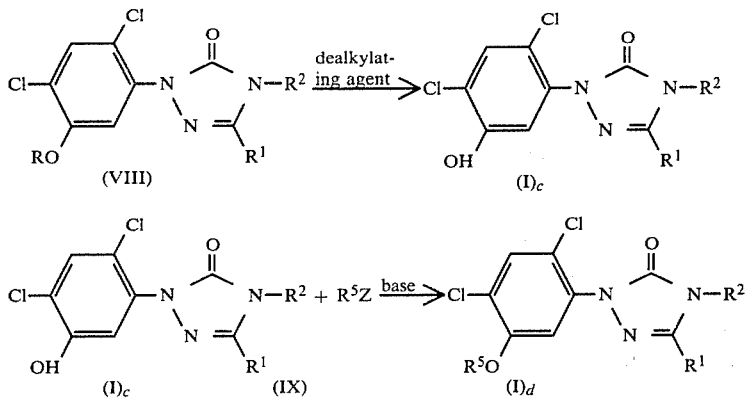

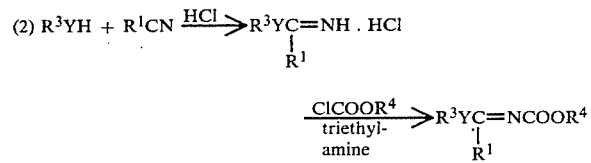

(wherein $R^1$, $R^3$, $R^4$ and Y are the same as defined above).

Process B:

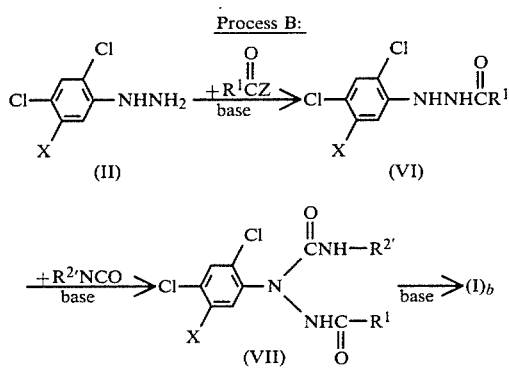

(wherein $R^1$, $R^{2'}$, X, and Z are the same as defined above).

That is, a compound of formula (I)$_b$ can be obtained by reacting a compound of (II) with an acylating agent, e.g., an acid halide in an inert solvent in the presence of a base, and reacting the resulting compound of (VI) with a carbamoyl group-introducing agent e.g., an isocyanate, followed by ring closure.

A compound of (VII) can also be obtained by reacting a compound of (VI) with phosgen and subsequently reacting with an amine represented by $R^{2'}NH_2$, where $R^{2'}$ is the same as defined above.

In this process, with or without isolation of a compound of (VI) or (VII) the next reaction can be carried out.

As the inert solvent and the base in this process, the same materials as enumerated in process A can be used, respectively; for the base used in obtaining a compound of (VII) from a compound of (VI), the organic bases enumerated in process A are particularly desirable, and for the base used in obtaining a compound of (I)$_b$ from a compound of (VII), caustic soda, caustic potash, and alkali metal alcolates such as sodium and potassium alcoholates are particularly desirable.

(wherein $R^1$, $R^2$, and Z are the same as defined above; $R^5$ is a $C_1$–$C_6$ alkyl, an alkyloxyalkyl of which two alkyls may be same or different and each alkyl is $C_1$–$C_4$ alkenyl, or an alkylcarbonylalkyl, of which two alkyls may be same or different and each alkyl is of $C_1$–$C_4$, and R is a $C_1$–$C_6$ alkyl or a $C_2$–$C_4$ alkenyl).

That is, a compound of (I)$_c$, which is one of the compounds of formula (I), can be obtained by reacting a compound of (VIII) with a dealkylating agent in an inert solvent.

Further, a compound of (I)$_d$, which is one of the compounds of formula (I), can be obtained by reacting a compound of (I)$_c$ with a compound of (I) in an inert solvent in the presence of a base.

As examples of the dealkylating agent used in this process, may be cited hydrobromic acid, hydrogen iodide, thioalkoxide, trimethylsilyl iodide, and boron trichloride, but the dealkylating agent is not limited to these compounds and may be any reagent that causes this type of dealkylation.

As the inert solvent for this reaction, those enumerated in process A can be used. In case of reacting a compound of (I)$_c$ and a compound of (IX), it is desirable to carry out the reaction in the presence of a base, though the reaction still proceeds in the absence of a base.

As the base for this reaction, the bases enumerated in process A can be used, but among them inorganic bases are preferable.

In all steps of these processes, reactions can be allowed to proceed in the range of from room temperature to 180° C.

Each reaction of these processes can be accomplished by using reactants in equimolar ration, but it is unobjectionable to use either one in slight excess. After the reaction has been completed, the objective material can be obtained through customary treatments of the reaction product. For example, it is accomplished by extracting the objective material from the reaction product with a suitable solvent, washing and drying the extract, and removing the solvent.

Typical examples of the compounds represented by formula (I) are shown in Table 1.

TABLE 1

| Compound No. | X | $R^1$ | $R^2$ | Melting point (°C.) or refractive index |
|---|---|---|---|---|
| 1 | $CH_3O$ | $CH_3$ | $CH_3$ | m.p. 170.4 |
| 2 | $CH_3O$ | $CH_3$ | $C_2H_5$ | m.p. 132.2 |
| 3 | $CH_3O$ | $CH_3$ | $i\text{-}C_3H_7$ | $n_D^{20}$ 1.5579 |
| 4 | $CH_3O$ | $CH_3$ | $CH_2=CH-CH_2$ | $n_D^{20}$ 1.5722 |
| 5 | $CH_3O$ | $CH_3$ | $n\text{-}C_4H_9$ | m.p. 93.3 |
| 6 | $CH_3O$ | $i\text{-}C_3H_7$ | H | m.p. 192.0 |
| 7 | $CH_3O$ | $i\text{-}C_3H_7$ | $CH_3$ | m.p. 137.0 |
| 8 | $CH_3O$ | $i\text{-}C_3H_7$ | $C_2H_5$ | m.p. 166.8 |
| 9 | $CH_3O$ | $i\text{-}C_3H_7$ | $CH_2=CH-CH_2$ | m.p. 86.0 |
| 10 | $CH_3O$ | $i\text{-}C_3H_7$ | $n\text{-}C_4H_9$ | m.p. 47.9 |
| 11 | $CH_3O$ | $t\text{-}C_4H_9$ | $CH_3$ | m.p. 152.1 |
| 12 | $C_2H_5O$ | $CH_3$ | H | m.p. 226.3 |
| 13 | $C_2H_5O$ | $CH_3$ | $CH_3$ | m.p. 133.2 |
| 14 | $C_2H_5O$ | $CH_3$ | $C_2H_5$ | m.p. 66.6 |
| 15 | $C_2H_5O$ | $CH_3$ | $i\text{-}C_3H_7$ | $n_D^{20}$ 1.5533 |
| 16 | $C_2H_5O$ | $CH_3$ | $CH_2=CH-CH_2$ | m.p. 71.7 |
| 17 | $C_2H_5O$ | $CH_3$ | $n\text{-}C_4H_9$ | $n_D^{20}$ 1.5500 |
| 18 | $C_2H_5O$ | $i\text{-}C_3H_7$ | H | m.p. 141.4 |
| 19 | $C_2H_5O$ | $i\text{-}C_3H_7$ | $CH_3$ | m.p. 121.4 |
| 20 | $C_2H_5O$ | $i\text{-}C_3H_7$ | $C_2H_5$ | m.p. 110.0 |
| 21 | $C_2H_5O$ | $i\text{-}C_3H_7$ | $CH_2=CH-CH_2$ | m.p. 77.8 |
| 22 | $C_2H_5O$ | $t\text{-}C_4H_9$ | $CH_3$ | m.p. 104.7 |
| 23 | $i\text{-}C_3H_7O$ | $CH_3$ | H | m.p. 165.7 |
| 24 | $i\text{-}C_3H_7O$ | $CH_3$ | $CH_3$ | m.p. 115.4 |
| 25 | $i\text{-}C_3H_7O$ | $CH_3$ | $C_2H_5$ | m.p. 68.1 |
| 26 | $i\text{-}C_3H_7O$ | $CH_3$ | $i\text{-}C_3H_7$ | $n_D^{25}$ 1.5418 |
| 27 | $i\text{-}C_3H_7O$ | $CH_3$ | $CH_2=CH-CH_2$ | $n_D^{25}$ 1.5573 |
| 28 | $i\text{-}C_3H_7O$ | $CH_3$ | $n\text{-}C_4H_9$ | $n_D^{25}$ 1.5432 |
| 29 | $i\text{-}C_3H_7O$ | $CH_3$ | $i\text{-}C_4H_9$ | $n_D^{22}$ 1.5428 |
| 30 | $i\text{-}C_3H_7O$ | $CH_3$ | $n\text{-}C_5H_{11}$ | $n_D^{22}$ 1.5422 |
| 31 | $i\text{-}C_3H_7O$ | $CH_3$ | $n\text{-}C_6H_{13}$ | $n_D^{22}$ 1.5395 |
| 32 | $i\text{-}C_3H_7O$ | $i\text{-}C_3H_7$ | H | m.p. 115.6 |
| 33 | $i\text{-}C_3H_7O$ | $i\text{-}C_3H_7$ | $CH_3$ | m.p. 104.5 |
| 34 | $i\text{-}C_3H_7O$ | $i\text{-}C_3H_7$ | $C_2H_5$ | m.p. 133.0 |
| 35 | $i\text{-}C_3H_7O$ | $i\text{-}C_3H_7$ | $i\text{-}C_3H_7$ | m.p. 143.5 |
| 36 | $i\text{-}C_3H_7O$ | $i\text{-}C_3H_7$ | $CH_2=CH-CH_2$ | m.p. 77.8 |
| 37 | $i\text{-}C_3H_7O$ | $i\text{-}C_3H_7$ | $n\text{-}C_4H_9$ | $n_D^{18}$ 1.5374 |
| 38 | $i\text{-}C_3H_7O$ | $t\text{-}C_4H_9$ | $CH_3$ | m.p. 112.5 |
| 39 | $CH_2=CH-CH_2O$ | $CH_3$ | H | m.p. 189.3 |
| 40 | $CH_2=CH-CH_2O$ | $CH_3$ | $CH_3$ | $n_D^{20}$ 1.5745 |
| 41 | $CH_2=CH-CH_2O$ | $CH_3$ | $C_2H_5$ | $n_D^{20}$ 1.5663 |
| 42 | $CH_2=CH-CH_2O$ | $CH_3$ | $i\text{-}C_3H_7$ | m.p. 72.2 |
| 43 | $CH_2=CH-CH_2O$ | $CH_3$ | $CH_2=CH-CH_2$ | $n_D^{20}$ 1.5730 |
| 44 | $CH_2=CH-CH_2O$ | $CH_3$ | $n\text{-}C_4H_9$ | $n_D^{20}$ 1.5597 |
| 45 | $CH_2=CH-CH_2O$ | $i\text{-}C_3H_7$ | H | m.p. 123.5 |
| 46 | $CH_2=CH-CH_2O$ | $i\text{-}C_3H_7$ | $CH_3$ | m.p. 76.4 |
| 47 | $CH_2=CH-CH_2O$ | $i\text{-}C_3H_7$ | $C_2H_5$ | m.p. 90.7 |
| 48 | $CH_2=CH-CH_2O$ | $i\text{-}C_3H_7$ | $CH_2=CH-CH_2$ | m.p. 59.0 |
| 49 | $CH_2=CH-CH_2O$ | $t\text{-}C_4H_9$ | $CH_3$ | m.p. 91.4 |
| 50 | $s\text{-}C_4H_9O$ | $CH_3$ | $C_2H_5$ | $n_D^{22}$ 1.5522 |
| 51 | $s\text{-}C_4H_9O$ | $CH_3$ | $CH_2=CH-CH_2$ | $n_D^{24}$ 1.5552 |
| 52 | $i\text{-}C_4H_9O$ | $CH_3$ | $CH_2=CH-CH_2$ | $n_D^{24}$ 1.5528 |
| 53 | $n\text{-}C_5H_{11}O$ | $CH_3$ | $C_2H_5$ | m.p. 67.1 |
| 54 | $n\text{-}C_5H_{11}O$ | $CH_3$ | $CH_2=CH-CH_2$ | $n_D^{22}$ 1.5536 |
| 55 | $n\text{-}C_6H_{13}O$ | $CH_3$ | $C_2H_5$ | $n_D^{22}$ 1.5455 |
| 56 | $n\text{-}C_6H_{13}O$ | $CH_3$ | $CH_2=CH-CH_2$ | $n_D^{22}$ 1.5497 |
| 57 | OH | $CH_3$ | $C_2H_5$ | m.p. 181.3 |
| 58 | OH | $CH_3$ | $CH_2=CH-CH_2$ | m.p. 138.8 |
| 59 | OH | $CH_3$ | $CH_3$ | m.p. 204.3 |
| 60 | OH | $CH_3$ | $n\text{-}C_4H_9$ | m.p. 146.6 |
| 61 | OH | $i\text{-}C_3H_7$ | $CH_3$ | m.p. 170.4 |
| 62 | $C_2H_5OCOCH(CH_3)-O$ | $CH_3$ | $C_2H_5$ | $n_D^{22}$ 1.5451 |
| 63 | $C_2H_5OCOCH(CH_3)O$ | $CH_3$ | $CH_2=CH-CH_2$ | $n_D^{22}$ 1.5459 |
| 64 | $CH_3OCOCH(CH_3)O$ | $CH_3$ | $CH_2=CH-CH_2$ | $n_D^{25}$ 1.5508 |
| 65 | $i\text{-}C_3H_7OCOCH(CH_3)O$ | $CH_3$ | $CH_2=CH-CH_2$ | $n_D^{25}$ 1.5389 |
| 66 | $CH_3$ | $CH_3$ | H | m.p. 222.2 |
| 67 | $CH_3$ | $CH_3$ | $CH_3$ | m.p. 162.9 |
| 68 | $CH_3$ | $CH_3$ | $C_2H_5$ | m.p. 146.6 |

TABLE 1-continued

| Compound No. | X | $R^1$ | $R^2$ | Melting point (°C.) or refractive index |
|---|---|---|---|---|
| 69 | $CH_3$ | $CH_3$ | $i-C_3H_7$ | $n_D^{25}$ 1.5598 |
| 70 | $CH_3$ | $CH_3$ | $CH_2=CH-CH_2$ | m.p. 89.4 |
| 71 | $CH_3$ | $i-C_3H_7$ | H | m.p. 221.0 |
| 72 | $CH_3$ | $i-C_3H_7$ | $CH_3$ | m.p. 92.9 |
| 73 | $CH_3$ | $i-C_3H_7$ | $C_2H_5$ | m.p. 133.5 |
| 74 | $CH_3$ | $i-C_3H_7$ | $CH_2=CH-CH_2$ | m.p. 54.5 |
| 75 | $CH_3$ | $t-C_4H_9$ | $CH_3$ | m.p. 82.0 |
| 76 | $C_2H_5OCH_2O$ | $CH_3$ | $CH_2=CH-CH_2$ | $n_D^{21}$ 1.5596 |
| 77 | $i-C_3H_7OCH_2O$ | $CH_3$ | $CH_2=CH-CH_2$ | $n_D^{21}$ 1.5514 |
| 78 | $n-C_4H_9OCH_2O$ | $CH_3$ | $CH_2=CH-CH_2$ | $n_D^{21}$ 1.5498 |
| 79 | $CH_3OCH_2CH_2O$ | $CH_3$ | $CH_2=CH-CH_2$ | $n_D^{21}$ 1.5610 |
| 80 | $C_2H_5OCH_2CH_2O$ | $CH_3$ | $CH_2=CH-CH_2$ | $n_D^{21}$ 1.5579 |
| 81 | $i-C_3H_7OCH_2CH_2O$ | $CH_3$ | $CH_2=CH-CH_2$ | $n_D^{21}$ 1.5487 |
| 82 | $CH_3OCH_2O$ | $CH_3$ | $C_2H_5$ | $n_D^{26}$ 1.5589 |
| 83 | $CH_3OCH_2O$ | $CH_3$ | $CH_3$ | m.p. 87.7 |
| 84 | $n-C_4H_9OCH_2O$ | $CH_3$ | $CH_3$ | $n_D^{25}$ 1.5496 |
| 85 | $n-C_3H_7OCH_2O$ | $CH_3$ | $CH_3$ | $n_D^{25}$ 1.5511 |
| 86 | $CH_3OCH_2CH_2O$ | $CH_3$ | $CH_3$ | m.p. 123.3 |
| 87 | $i-C_3H_7OCH_2CH_2O$ | $CH_3$ | $CH_3$ | m.p. 106.9 |
| 88 | $CH_3OCH_2O$ | $CH_3$ | $n-C_4H_9$ | $n_D^{25}$ 1.5492 |
| 89 | $C_2H_5OCH_2CH_2O$ | $CH_3$ | $n-C_4H_9$ | $n_D^{25}$ 1.5410 |
| 90 | $CH_3OCH_2O$ | $i-C_3H_7$ | $CH_3$ | m.p. 104.7 |
| 91 | $i-C_3H_7OCH_2O$ | $i-C_3H_7$ | $CH_3$ | m.p. 65.6 |
| 92 | $CH_3OCH_2CH_2O$ | $i-C_3H_7$ | $CH_3$ | $n_D^{25}$ 1.5516 |
| 93 | $CH_3OCH_2O$ | $CH_3$ | $CH_2=CH-CH_2$ | $n_D^{24}$ 1.5630 |
| 94 | OH | $CH_3$ | H | m.p. 275.1 |
| 95 | OH | $i-C_3H_7$ | H | m.p. 289.9 |

These $\Delta^2$-1,2,4-triazolin-5-one derivatives are capable of controlling annual and perennial weeds grown in paddy fields, upland fields, orchards, and swamps, such as barnyard grass (Echinochloa Crusgalli Beauv, an annual gramineous grass which is a typical weed grown in paddy fields and strongly injurious), monochoria (Monochoria vaginalis Presl, a strongly injurious annual weed of Pontederiaceae family grown in paddy fields), umbrella plant (Cyperus difformis L., an injurious annual cyperaceous weed grown in paddy fields), slender spikerush (Eleocharis acicularis Roem. et Schult, a typical injurious perennial cyperaceous weed of paddy fields, grown also in swamps and waterways), Arrowhead (Sagittaria pygmaea Miq., an injurious perennial weed of Alismataceae family, grown in paddy fields, swamps, and ditches), bulrush (Scirpus juncoides Roxb. var. hotarui ohwi., a annual cyperaceous weed grown in paddy fields, swamps, and ditches), wild oats (Avena fatua L., an annual gramineous grass grown in plains, waste lands, and upland fields), mugwort (Artemisia princeps Pamp., a perennial composite grass grown in cultivated and uncultivated fields and mountains), large crabgrass (Digitaria adscendcus Henr., an annual gramineous grass which is a typical strongly injurious weed gronw in upland fields and orchards), Gishi-gishi (Rumex japonicus Houtt, a perennial polygonaceous weed grown in upland fields and on roadsides), umbrella sedge (Cyperus Iria L., an annual cyperaceous weed grown in upland fields and on roadsides), and Redroot pigweed (Amaranthus varidis L., an annual weed of Amaranthaceae family grown in upland fields, vacant lands, and roadsides).

Since the compounds represented by formual (I) exhibit an excellent controlling action against weeds in the prior and initial stages of emergence, their characteristic physiological activities can be manifested more effectively by treating fields with the compounds before planting useful plants therein, after planting useful plants therein (including fields such as orchards, where useful plants have already planted) but before the emergence of weeds, or after sowing of useful plants but before the emergence of the plants. However, the application mode of the present herbicides is not limited only to those described above; they can also be used as a herbicide appling at middle stage of rice for paddy fields and moreover, as a herbicide to control general weeds grown in, for example, reaped fields, temporarily non-cultivated fields, ridges between paddy fields, agricultrual pathways, waterways, fields constructed for pasture, graveyards, parks, roads, playgrounds, unoccupied areas around buildings, reclaimed lands, railways, and forests. Herbicidal treatment of such areas is carried out most effectively and economically but not necessarily prior to the emergence of weeds.

For applying the present compounds as a herbicide, they are generally made up, according to the customary procedure for preparing agricultural chemicals, into a form convenient to use. That is, the present compounds are blended with suitable inert carriers and, if necessary, further with adjuvants, in a suitable ratio, and through dissolution, dispersion, suspension, mechanical mixing, impregnation, adsorption, or adhesion, a suitable form of preparation, e.g., suspensions, emulsifiable concentrates, solutions, wettable powders, dusts, granules, or tablets may be obtained.

The inert carriers to be used in the formulations may be either solids or liquids. As examples of the adaptable solid carriers, may be cited vegetable powders such as soybean flour, cereal flour, wood flour, bark flour, saw dust, powdered tabaco stalk, powdered walnut sheel, bran, powdered cellulose, and extraction residues of vegetables; fibrous materials such as paper, corrugated paperboard, and waste cloth; synthetic polymers such as powdered synthetic resins; inorganic or mineral products such as clays (e,g,, kaolin, bentonite, and acid clay), talcs (e.g., talc and pyrophillite), siliceous substances [e.g., diatomaceous earth, silica sand, mica, and "white carbon" (highly dispersed synthetic silicic acid, also called finely devided hydrated silica or hydrated silicic acid; some commercial products contain calcium silicate as major constituent)], activated carbon, powdered sulfur, pumice, calcined diatomaceous earth, ground brick, fly ash, sand, calcium carbonate, and calcium phosphate; chemical fertilizers such as ammonium sulfate, ammonium nitrate, urea, and ammonium chloride; and farmyard manure. These materials are used each alone or in combination with one another. The material usuable as liquid carriers are selected from those which are solvents for the active compounds and those which are non-solvent but can disperse the active compounds with the aid of adjuvants. For example, the following materials can be used each alone or in combination with one another: water, alcohols (e.g., methanol, ethanol, isopropanol, butanol, ehtylene glycol), ketones (e.g., acetone, methyl ethyl ketone, methyl isobutyl ketone, diisobutyl ketone, and cylohexanone), ethers (e.g., ethyl ether, dioxane, cellosolves, dipropyl ether, and tetrahydrofuran), aliphatic hydrocarbons (e.g., gasoline and mineral oils), aromatic hydrocarbons (e.g., benzene, toluene, xylene, solvent napththa, and alkylnapthalenes), halohydrocarbons (e.g., dichloroethane, chlorinated benzenes, chloroform, and carbon tetrachloride), esters (e.g., ethyl acetate, dibutyl phthalate, diisopropyl phthalate, and dioctyl phthalate), acid amides (e.g., dimethylformamide, diethylformamide, and dimethylacetamide), nitriles (e.g., acetonitrile), and dimethyl sulfoide.

The adjuvants, which are exemplified below, are used according to individual purposes. In some cases, they are used in combination with one another. In some other cases, no adjuvant is used at all.

For the purpose of emulsification, dispersion, solubilization and/or wetting of the active compounds, are used surface active agents, for example, polyoxyethylene alkylaryl ethers, polyoxyethylene alkyl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates, and higher alcohol sulfate esters.

For the purpose of stabilizing the dispersion, tackification, and/or agglomeration of the active compounds, may be used, for example, casein, gelatin, starch, alginic acid, methylcellulose, carboxymethylcellulose, gum arabic, polyvinyl alcohol, turpentine oil, rice bran oil, bentonite, and ligninsulfonates.

For the purpose of improving the flow property of the solid composition, it is recommendable to use waxes, stearates, or alkyl phosphates.

As peptizers for a dispersible composition, it is also recommendable to use naphthalenesulfonic acid condensation products and polyphosphates.

It is also possible to add a defoamer such as, for example, a silicone oil.

The content of the active ingredient may be adjusted as occasion demands; for the preparation of powdered or granulated products, it is usually 0.5 to 20% by weight, and for the preparation of emulsifiable concentrates or wettable powder products, it is desirably 0.1 to 50% by weight.

For destroying various weeds, inhibiting their growth, or protecting useful plants from the injury caused by weeds, a weed-destroying dosage or a weed growth-inhibiting dosage of the present herbicidal composition is applied as such or after properly diluted with or suspended in water or in other suitable medium, to the soil or the foilage of weeds in the area where the emergence or growth of weeds is undesirable.

The amount of the present herbicide to be used depends on various factors such as, for example, the purpose of application, objective weeds, the emergence or growth state of weeds and crops, the emergence tendency of weeds, weather, environmental conditions, the form of the herbicide composition, the mode of application, the type of the field to be treated, and the time of application.

In applying the present herbicidal composition alone as a selective herbicide, it is suitable to select the dosage of the present active compound from the range of 10 to 500 g per 10 ares. Considering that, in the combined use of herbicides, the optimum dosage thereof is often lower than that in the single use, the present herbicide may be used in an amount lower than the above, when it is used in combination with another sort of herbicide.

The present herbicide is especially valuable for the pre-emergence treatment and initial emergence stage treatment of upland fields and for the early stage and middle stage control of weeds in paddy fields. In order to expand both the range of controllable weed species and the period of time when effective applications are possible or to reduce the dosage, the present herbicides can be used in combination with other herbicides, and this usage is within the scope of this invention. For example, the present herbicide can be used in combination with one or more of the following herbicides: phenoxy fatty acid group herbicides such as 2.4-PA's (e.g., 2,4-dichlorophenoxyacetate), MCP's (e.g., ethyl 2-methyl-4-chlorophenoxyacetate, sodium 2-methyl-4-chlorophenoxyacetate, and ally 2-methyl-4-chlorophenoxyacetate), MCPB (ethyl 2-methyl-4-chlorophenoxybutyrate); diphenyl ether group herbicides such as NIP (2,4-dichlorophenyl 4'-nitrophenyl ether), CNP (2,4,6-trichlorophenyl 4'-nitrophenyl ether), and Chlomethoxynic (2,4-dichlorophenyl 3'-methoxy-4'-nitrophenyl ether); s-triazine group herbicides such as CAT [2-chloro-4,6-bis(ethylamino)-s-triazine], Prometryne [2-methylthio-4,6-bis(isopropylamino)-s-triazine], and Simetryne [2-methylthio-4,6-bis(ethylamino)-s-triazine]; carbamate group herbicide such as Molinate (S-ethylhexahydro-1H-azepin-1-carbothioate), MCC [methyl N-(3,4-dichlorophenyl) carbamate], IPC [isopropyl N-(3-chlorophenyl) carbamate], Benthiocarb [S-(4-chlorobenzyl)N,N-diethylthiocarbamate]; and other herbicides such as DCPA (3,4-dichloropropionanilide), Butachlor (2-chloro-2',6'-diethyl-N-(butoxymethyl)-acetanilide], Alachlor (2-chloro-2',6'-diethyl-N-(methoxymethyl)acetanilide], Bentazon [3-isopropyl-2,1,3-benzothiadiazinone-(4)-2,2-dioxide], trifluralin ($\alpha,\alpha,\alpha$-trifluoro-2,6-dinitro-N,N-dipropyl-p-toluidine), and DCMU [3-(3,4-dichlorophenyl)-1,1-dimethylurea]. The above abbreviations conform to the description in "Pesticide Manual, 1978" published by Japan Plant Protection Association.

The following examples illustrate the herbicidal effect, the formulations, and the process of synthesis of the compounds of this invention, but the invention is not to be limited to these examples.

TEST EXAMPLE 1

Controlling effect on paddy field weeds of pre-emergence stage

Pots (1/10,000—are) were filled with soil to simulate a paddy field, and planted with seeds of barnyard grass, monochoria, umbrella plant, and hotarui, and with tubers of arrowhead, respectively, which are all injurious weeds grown in paddy fields, were conditioned so as to be in a pre-emergence stage.

The soil in the pots was treated with each of the present active compounds (listed in Table 1) formulated to a given concentration of liquid, by spraying. After 21 days, the percent control of weed growth compared with that on the untreated plot was evaluated and the herbicial activity was judged according to the following criterion.

Criterion for judging herbicidal activity

| Degree of herbicidal activity | Percent control of weed growth (%) |
|---|---|
| 5 | 100 |
| 4 | 90–99 |
| 3 | 80–89 |
| 2 | 70–79 |
| 1 | <70 |

The results were summarized in Table 2.

TABLE 2

| Compound No. | Amount of active ingredient applied (g/are) | Effect of pre-emergence treatment | | | | |
|---|---|---|---|---|---|---|
| | | Barnyard grass | Monochoria | Umbrella plant | Hotarui | Arrowhead |
| 1 | 50 | 4 | 5 | 5 | 3 | 5 |
| 2 | 50 | 5 | 5 | 5 | 4 | 4 |
| 3 | 50 | 5 | 5 | 5 | 4 | 5 |
| 4 | 50 | 5 | 5 | 5 | 4 | 5 |
| 5 | 50 | 5 | 5 | 5 | 3 | 5 |
| 6 | 50 | 4 | 5 | 5 | 2 | 4 |
| 7 | 50 | 5 | 5 | 5 | 4 | 5 |
| 8 | 50 | 5 | 5 | 5 | 4 | 5 |
| 9 | 50 | 5 | 5 | 5 | 3 | 5 |
| 10 | 50 | 4 | 5 | 5 | 2 | 5 |
| 11 | 50 | 5 | 5 | 5 | 5 | 5 |
| 12 | 50 | 2 | 4 | 5 | 2 | 2 |
| 13 | 50 | 5 | 5 | 5 | 4 | 5 |
| 14 | 50 | 5 | 5 | 5 | 4 | 5 |
| 15 | 50 | 5 | 5 | 5 | 4 | 5 |
| 16 | 50 | 5 | 5 | 5 | 5 | 5 |
| 17 | 50 | 5 | 5 | 5 | 4 | 5 |
| 18 | 50 | 3 | 5 | 5 | 3 | 3 |
| 19 | 50 | 5 | 5 | 5 | 5 | 5 |
| 20 | 50 | 5 | 5 | 5 | 5 | 5 |
| 21 | 50 | 5 | 5 | 5 | 3 | 5 |
| 22 | 50 | 5 | 5 | 5 | 5 | 5 |
| 24 | 50 | 5 | 5 | 5 | 5 | 5 |
| 25 | 50 | 5 | 5 | 5 | 5 | 5 |
| 26 | 50 | 5 | 5 | 5 | 5 | 5 |
| 27 | 50 | 5 | 5 | 5 | 5 | 5 |
| 28 | 50 | 5 | 5 | 5 | 4 | 5 |
| 32 | 50 | 5 | 5 | 5 | 4 | 5 |
| 33 | 50 | 5 | 5 | 5 | 5 | 5 |
| 34 | 50 | 5 | 5 | 5 | 5 | 5 |
| 35 | 50 | 2 | 4 | 5 | 3 | 2 |
| 36 | 50 | 5 | 5 | 5 | 4 | 4 |
| 37 | 50 | 5 | 5 | 5 | 4 | 5 |
| 38 | 50 | 5 | 5 | 5 | 4 | 5 |
| 39 | 50 | 2 | 4 | 5 | 2 | 2 |
| 40 | 50 | 5 | 5 | 5 | 4 | 5 |
| 41 | 50 | 5 | 5 | 5 | 5 | 5 |
| 42 | 50 | 5 | 5 | 5 | 5 | 5 |
| 43 | 50 | 5 | 5 | 5 | 4 | 5 |
| 44 | 50 | 5 | 5 | 5 | 4 | 5 |
| 45 | 50 | 4 | 5 | 5 | 2 | 3 |
| 46 | 50 | 5 | 5 | 5 | 4 | 5 |
| 47 | 50 | 5 | 5 | 5 | 5 | 5 |
| 48 | 50 | 5 | 5 | 5 | 3 | 5 |
| 50 | 50 | 5 | 5 | 5 | 4 | 3 |
| 51 | 50 | 5 | 5 | 5 | 5 | 5 |
| 52 | 50 | 5 | 5 | 5 | 5 | 5 |
| 53 | 50 | 5 | 5 | 5 | 3 | 3 |
| 54 | 50 | 5 | 5 | 5 | 5 | 2 |
| 55 | 50 | 5 | 5 | 5 | 4 | 2 |
| 56 | 50 | 5 | 5 | 5 | 3 | 2 |
| 57 | 50 | 5 | 5 | 5 | 5 | 5 |
| 62 | 50 | 3 | 5 | 5 | 3 | 5 |
| 63 | 50 | 5 | 5 | 5 | 4 | 5 |
| 64 | 50 | 5 | 5 | 5 | 5 | 5 |
| 65 | 50 | 5 | 5 | 5 | 4 | 5 |
| 67 | 50 | 5 | 5 | 5 | 3 | 2 |
| 68 | 50 | 5 | 5 | 5 | 4 | 5 |
| 69 | 50 | 5 | 5 | 5 | 4 | 5 |
| 70 | 50 | 5 | 5 | 5 | 4 | 5 |
| 71 | 50 | 3 | 5 | 5 | 2 | 2 |
| 72 | 50 | 5 | 5 | 5 | 4 | 5 |
| 73 | 50 | 5 | 5 | 5 | 4 | 3 |
| 74 | 50 | 3 | 5 | 5 | 2 | 2 |
| 75 | 50 | 5 | 5 | 5 | 4 | 5 |
| 76 | 50 | 5 | 5 | 5 | 5 | 5 |
| 77 | 50 | 5 | 5 | 5 | 4 | 5 |
| 78 | 50 | 5 | 5 | 5 | 4 | 4 |
| 79 | 50 | 5 | 5 | 5 | 5 | 5 |
| 80 | 50 | 5 | 5 | 5 | 4 | 5 |
| 81 | 50 | 5 | 5 | 5 | 5 | 4 |
| 82 | 50 | 5 | 5 | 5 | 5 | 5 |
| 83 | 50 | 5 | 5 | 5 | 5 | 5 |
| 84 | 50 | 5 | 5 | 5 | 4 | 4 |
| 85 | 50 | 4 | 5 | 5 | 3 | 2 |
| 86 | 50 | 4 | 4 | 5 | 2 | 2 |
| 87 | 50 | 4 | 4 | 5 | 2 | 2 |
| 88 | 50 | 5 | 5 | 5 | 5 | 5 |
| 89 | 50 | 4 | 5 | 5 | 4 | 4 |
| 90 | 50 | 5 | 5 | 5 | 5 | 5 |
| 91 | 50 | 5 | 4 | 5 | 5 | 5 |
| 92 | 50 | 5 | 5 | 5 | 5 | 5 |
| 93 | 50 | 5 | 5 | 5 | 5 | 5 |

TEST EXAMPLE 2

Controlling effect on paddy field weeds of post-emergence stage

Pots (1/10,000-are) were filled with soil to simulate a paddy field and grown with each of injurious weeds of the following leaf age. In addition, young seedlings of rice plant (cultivar "Niphonbare") of the 2.5 leaf age were transplanted to the soil on the day before the treatment with each of the present herbicides. After 21 days from the treatment, the herbicidal effect and the degree of crop injury were evaluated by comparing the results with those on the untreated plot.

| Species of sample weed | Leaf age of weed |
|---|---|
| Barnyard grass | 1 |
| Monochoria | 2–3 |
| Umbrella plant | 1–2 |
| Hotarui | 2–3 |
| Arrowhead | 3 |

| Criterion for judging degree of chemical injury |
|---|
| H : High (including withering) |
| M : Medium |
| L : Low |
| N : None |

The criterion for judging the herbicidal activity is in accordance with Test Example 1. The results were summarized in Table 3.

TABLE 3

| Compound No. | Amount of active ingredient applied (g/are) | Effect of post-emergence treatment | | | | | Chemical injury Paddy rice |
|---|---|---|---|---|---|---|---|
| | | Barnyard grass | Monochoria | Umbrella plant | hotarui | Arrowhead | |
| 1 | 50 | 5 | 4 | 4 | 2 | 2 | N |
| 2 | 50 | 5 | 4 | 5 | 3 | 3 | L |
| 3 | 50 | 5 | 3 | 3 | 2 | 3 | L |
| 4 | 50 | 5 | 4 | 5 | 3 | 3 | L |
| 5 | 50 | 5 | 4 | 4 | 2 | 2 | L |
| 7 | 50 | 5 | 4 | 5 | 4 | 5 | L |
| 8 | 50 | 5 | 3 | 4 | 2 | 3 | N |
| 9 | 50 | 5 | 3 | 2 | 2 | 2 | L |
| 10 | 50 | 5 | 2 | 2 | 2 | 2 | N |
| 11 | 50 | 5 | 4 | 5 | 3 | 3 | L |
| 13 | 50 | 5 | 3 | 5 | 2 | 2 | L |
| 14 | 50 | 5 | 4 | 5 | 2 | 2 | L |
| 15 | 50 | 5 | 3 | 4 | 2 | 4 | L |
| 16 | 50 | 5 | 4 | 5 | 3 | 3 | L |
| 17 | 50 | 5 | 2 | 3 | 2 | 2 | N |
| 24 | 50 | 5 | 4 | 5 | 4 | 4 | L |
| 25 | 50 | 5 | 4 | 5 | 3 | 5 | L |
| 26 | 50 | 5 | 4 | 4 | 2 | 5 | L |
| 27 | 50 | 5 | 4 | 5 | 3 | 5 | L |
| 28 | 50 | 5 | 4 | 4 | 2 | 4 | L |
| 32 | 50 | 4 | 5 | 5 | 4 | 4 | N |
| 33 | 50 | 5 | 5 | 5 | 5 | 5 | L |
| 34 | 50 | 5 | 5 | 5 | 5 | 5 | L |
| 36 | 50 | 5 | 5 | 5 | 4 | 4 | N |
| 37 | 50 | 4 | 4 | 5 | 4 | 2 | N |
| 38 | 50 | 5 | 4 | 4 | 3 | 5 | L |
| 40 | 50 | 5 | 4 | 5 | 3 | 3 | L |
| 41 | 50 | 5 | 4 | 3 | 2 | 3 | L |
| 42 | 50 | 5 | 4 | 4 | 3 | 3 | L |
| 43 | 50 | 5 | 3 | 5 | 2 | 3 | L |
| 44 | 50 | 5 | 3 | 3 | 2 | 2 | L |
| 46 | 50 | 5 | 3 | 2 | 2 | 2 | L |
| 49 | 50 | 5 | 4 | 5 | 2 | 3 | L |
| 51 | 50 | 5 | 4 | 4 | 3 | 2 | L |
| 52 | 50 | 5 | 3 | 5 | 2 | 3 | L |
| 53 | 50 | 5 | 3 | 2 | 2 | 2 | N |
| 54 | 50 | 5 | 2 | 5 | 2 | 2 | N |
| 56 | 50 | 5 | 2 | 3 | 2 | 2 | N |
| 57 | 50 | 5 | 3 | 5 | 2 | 3 | L |
| 63 | 50 | 5 | 3 | 3 | 2 | 4 | N |
| 64 | 50 | 2 | 4 | 4 | 2 | 2 | N |
| 65 | 50 | 4 | 4 | 4 | 2 | 3 | N |
| 67 | 50 | 5 | 4 | 4 | 2 | 2 | L |
| 68 | 50 | 5 | 3 | 2 | 2 | 2 | L |
| 69 | 50 | 5 | 3 | 3 | 2 | 3 | L |
| 70 | 50 | 5 | 4 | 4 | 2 | 3 | L |
| 72 | 50 | 5 | 4 | 5 | 4 | 3 | L |
| 73 | 50 | 5 | 3 | 4 | 2 | 2 | L |
| 75 | 50 | 5 | 4 | 5 | 2 | 2 | L |
| 76 | 50 | 5 | 4 | 4 | 2 | 3 | L |
| 77 | 50 | 5 | 4 | 4 | 3 | 3 | L |
| 78 | 50 | 5 | 4 | 4 | 2 | 2 | N |
| 79 | 50 | 5 | 4 | 2 | 2 | 3 | L |
| 80 | 50 | 5 | 4 | 4 | 2 | 3 | L |
| 81 | 50 | 5 | 4 | 4 | 2 | 3 | L |
| 82 | 50 | 5 | 4 | 4 | 4 | 5 | L |
| 83 | 50 | 5 | 3 | 4 | 2 | 3 | L |
| 84 | 50 | 5 | 3 | 5 | 2 | 2 | N |
| 85 | 50 | 4 | 3 | 3 | 2 | 2 | L |
| 86 | 50 | 4 | 3 | 4 | 2 | 2 | L |
| 87 | 50 | 4 | 3 | 4 | 2 | 2 | L |
| 88 | 50 | 5 | 4 | 4 | 2 | 3 | L |
| 89 | 50 | 4 | 3 | 3 | 2 | 2 | L |
| 90 | 50 | 5 | 4 | 5 | 2 | 2 | L |
| 91 | 50 | 5 | 3 | 3 | 2 | 3 | L |
| 92 | 50 | 5 | 3 | 5 | 2 | 2 | L |
| 93 | 50 | 5 | 4 | 5 | 3 | 3 | L |

TEST EXAMPLE 3

Controlling effect on upland field weeds of pre-emergence stage

Polyethylene vats, 10 cm×20 cm×5 cm (depth), were filled with soil and seeded with oats, barnyard grass, large crabgrass, redroot pigweed, mugwort, Gi-shi-gishi and umbrella sedge, respectively, and seeds were covered with soil.

The soil was treated with each of the present active compounds formulated to a given concentration of liquid, by spraying. After 21 days, the herbicidal effect was evaluated by comparing the results with those on the untreated plot. The criterion for judging the herbicidal activity is in accordance with Test Example 1. The results were summerized in Table 4.

TABLE 4

| Compound No. | Amount of active ingredient applied (g/are) | Effect of pre-emergence treatment | | | | | | |
|---|---|---|---|---|---|---|---|---|
| | | Oats | Barnyard grass | Large crabgrass | Redroot pigweed | Mugwort | Gishi-gishi | Umbrella sedge |
| 1 | 50 | 3 | 3 | 5 | 5 | 5 | 5 | 5 |
| 2 | 50 | 4 | 5 | 5 | 5 | 5 | 5 | 5 |
| 3 | 50 | 3 | 4 | 5 | 5 | 5 | 5 | 5 |
| 4 | 50 | 4 | 4 | 5 | 5 | 5 | 5 | 5 |
| 5 | 50 | 2 | 4 | 4 | 5 | 4 | 5 | 5 |
| 6 | 50 | 3 | 3 | 5 | 5 | 2 | 4 | 5 |
| 7 | 50 | 3 | 5 | 5 | 5 | 5 | 5 | 5 |
| 8 | 50 | 3 | 3 | 5 | 5 | 3 | 5 | 5 |
| 9 | 50 | 3 | 3 | 4 | 5 | 3 | 5 | 5 |
| 10 | 50 | 3 | 3 | 4 | 5 | 3 | 5 | 5 |
| 11 | 50 | 5 | 5 | 5 | 5 | 5 | 5 | 5 |
| 13 | 50 | 3 | 4 | 5 | 5 | 5 | 5 | 5 |
| 14 | 50 | 4 | 4 | 5 | 5 | 5 | 5 | 5 |
| 15 | 50 | 3 | 4 | 5 | 5 | 5 | 5 | 5 |
| 16 | 50 | 3 | 5 | 5 | 5 | 5 | 5 | 5 |
| 17 | 50 | 2 | 3 | 5 | 5 | 5 | 5 | 4 |
| 18 | 50 | 2 | 2 | 4 | 5 | 4 | 4 | 5 |
| 19 | 50 | 3 | 5 | 5 | 5 | 5 | 5 | 5 |
| 20 | 50 | 3 | 3 | 5 | 5 | 5 | 5 | 5 |
| 21 | 50 | 2 | 2 | 4 | 5 | 4 | 5 | 5 |
| 22 | 50 | 2 | 5 | 5 | 5 | 5 | 5 | 5 |
| 24 | 50 | 5 | 5 | 5 | 5 | 5 | 5 | 5 |
| 25 | 25 | 3 | 5 | 5 | 5 | 5 | 5 | 5 |
| 26 | 50 | 5 | 5 | 5 | 5 | 5 | 5 | 5 |
| 27 | 50 | 5 | 5 | 5 | 5 | 5 | 5 | 5 |
| 28* | 50 | 4 | 4 | 5 | 5 | 5 | 5 | 5 |
| 29 | 50 | 2 | 5 | 5 | 5 | 5 | 5 | 5 |
| 30 | 50 | 2 | 2 | 2 | 5 | 5 | 4 | 5 |
| 31 | 50 | 2 | 2 | 3 | 5 | 5 | 4 | 5 |
| 32 | 50 | 2 | 2 | 5 | 5 | 4 | 5 | 5 |
| 33 | 50 | 4 | 4 | 5 | 5 | 5 | 5 | 5 |
| 34 | 50 | 3 | 3 | 5 | 5 | 2 | 5 | 5 |
| 36 | 50 | 2 | 2 | 5 | 5 | 2 | 5 | 5 |
| 37 | 50 | 2 | 2 | 5 | 4 | 2 | 5 | 5 |
| 38 | 50 | 5 | 5 | 5 | 5 | 5 | 5 | 5 |
| 40 | 50 | 3 | 5 | 5 | 5 | 5 | 5 | 5 |
| 41 | 50 | 4 | 5 | 5 | 5 | 5 | 5 | 5 |
| 42 | 50 | 3 | 4 | 5 | 5 | 5 | 5 | 5 |
| 43 | 50 | 5 | 5 | 5 | 5 | 5 | 5 | 5 |
| 44 | 50 | 2 | 5 | 5 | 5 | 5 | 5 | 5 |
| 46 | 50 | 5 | 5 | 5 | 5 | 5 | 5 | 5 |
| 47 | 50 | 3 | 5 | 5 | 5 | 3 | 5 | 5 |
| 48 | 50 | 2 | 4 | 5 | 5 | 2 | 5 | 5 |
| 49 | 50 | 2 | 5 | 5 | 5 | 5 | 5 | 5 |
| 50 | 50 | 5 | 5 | 5 | 5 | 5 | 5 | 5 |
| 51 | 50 | 4 | 5 | 5 | 5 | 5 | 5 | 5 |
| 52 | 50 | 3 | 4 | 5 | 5 | 5 | 5 | 5 |
| 53 | 50 | 2 | 4 | 5 | 5 | 5 | 5 | 5 |
| 54 | 50 | 2 | 4 | 5 | 5 | 5 | 4 | 5 |
| 55 | 50 | 2 | 2 | 5 | 5 | 4 | 5 | 5 |
| 56 | 50 | 2 | 2 | 5 | 5 | 2 | 2 | 5 |
| 57 | 50 | 2 | 2 | 2 | 5 | 2 | 2 | 5 |
| 62 | 50 | 2 | 2 | 5 | 5 | 5 | 4 | 5 |
| 63 | 50 | 2 | 4 | 5 | 5 | 5 | 5 | 5 |
| 64 | 50 | 2 | 3 | 5 | 5 | 5 | 4 | 5 |
| 65 | 50 | 2 | 3 | 5 | 5 | 5 | 5 | 5 |
| 67 | 50 | 2 | 5 | 5 | 4 | 3 | 5 | 5 |
| 68 | 50 | 3 | 5 | 5 | 5 | 5 | 5 | 5 |
| 69 | 50 | 2 | 4 | 5 | 4 | 5 | 5 | 5 |
| 70 | 50 | 5 | 5 | 5 | 5 | 5 | 5 | 5 |
| 71 | 50 | 2 | 3 | 4 | 5 | 2 | 4 | 2 |
| 72 | 50 | 3 | 5 | 5 | 5 | 5 | 5 | 5 |
| 73 | 50 | 2 | 5 | 5 | 5 | 2 | 5 | 5 |
| 74 | 50 | 2 | 4 | 5 | 5 | 2 | 4 | 5 |
| 75 | 50 | 2 | 3 | 5 | 4 | 2 | 5 | 5 |
| 76 | 50 | 4 | 5 | 5 | 5 | 5 | 5 | 5 |
| 77 | 50 | 4 | 5 | 5 | 5 | 5 | 5 | 5 |
| 78 | 50 | 3 | 3 | 5 | 5 | 5 | 5 | 5 |
| 79 | 50 | 4 | 5 | 5 | 5 | 5 | 5 | 5 |
| 80 | 50 | 4 | 5 | 5 | 5 | 5 | 5 | 5 |
| 81 | 50 | 2 | 4 | 5 | 5 | 5 | 5 | 5 |
| 82 | 50 | 5 | 5 | 5 | 5 | 5 | 5 | 5 |

TABLE 4-continued

| Compound No. | Amount of active ingredient applied (g/are) | Effect of pre-emergence treatment | | | | | | |
|---|---|---|---|---|---|---|---|---|
| | | Oats | Barnyard grass | Large crabgrass | Redroot pigweed | Mugwort | Gishi-gishi | Umbrella sedge |
| 83 | 50 | 4 | 5 | 5 | 5 | 5 | 5 | 5 |
| 84 | 50 | 2 | 4 | 5 | 5 | 5 | 5 | 5 |
| 85 | 50 | 3 | 4 | 5 | 5 | 5 | 5 | 5 |
| 86 | 50 | 3 | 4 | 5 | 5 | 5 | 5 | 5 |
| 87 | 50 | 2 | 5 | 5 | 5 | 5 | 4 | 5 |
| 88 | 50 | 4 | 5 | 5 | 5 | 5 | 5 | 5 |
| 89 | 50 | 4 | 4 | 5 | 5 | 5 | 5 | 5 |
| 90 | 50 | 5 | 5 | 5 | 5 | 5 | 5 | 5 |
| 91 | 50 | 5 | 5 | 5 | 5 | 5 | 5 | 5 |
| 92 | 50 | 4 | 5 | 5 | 5 | 5 | 5 | 5 |
| 93 | 50 | 5 | 5 | 5 | 5 | 5 | 5 | 5 |

TEST EXAMPLE 4

Controlling effect on upland field weeds of post-emergence stage

Polyethylene vats, 10 cm×20 cm×5 cm (depth), were filled with soil and seeded with the weeds shown below and soybean seeds, respectively, and the seeds were covered with soil. The weeds and soybean were cultivated respectively to the following leaf ages and then treated with each of the present active compounds at a given dosage.

After 21 days, the herbicidal effect on the weeds and the degree of crop injury to the soybean were evaluated by comparing the results with those on the untreated plot.

| Species of sample plant | Leaf age of sample plant |
|---|---|
| Oats | 2 |
| Large crabgrass | 2 |
| Redroot pigweed | 1 |
| Mugwort | 1 |
| Gishi-gishi | 2 |
| Umbrella sedge | 1 |
| Soybean | First double leaf age |

The criteria for judging the herbicidal activity and chemical injury were in accordance with Test Examples 1 and 2, respectively. The results were summerized in Table 5.

TABLE 5

| Compound No. | Amount of active ingredient applied (g/are) | Effect of post-emergence treatment | | | | | | Chemical injury Soybean |
|---|---|---|---|---|---|---|---|---|
| | | Oats | Large crabgrass | Redroot pigweed | Mugwort | Gishi-gishi | Umbrella sedge | |
| 1 | 50 | 3 | 2 | 5 | 2 | 4 | 2 | L |
| 2 | 50 | 3 | 3 | 5 | 4 | 2 | 4 | L |
| 3 | 50 | 4 | 2 | 5 | 4 | 5 | 5 | L |
| 4 | 50 | 4 | 4 | 5 | 3 | 5 | 5 | L |
| 5 | 50 | 3 | 4 | 5 | 2 | 4 | 5 | L |
| 7 | 50 | 4 | 3 | 5 | 2 | 4 | 5 | N |
| 8 | 50 | 3 | 2 | 3 | 2 | 2 | 3 | N |
| 9 | 50 | 3 | 4 | 5 | 2 | 3 | 2 | N |
| 10 | 50 | 3 | 4 | 5 | 2 | 3 | 2 | N |
| 11 | 50 | 3 | 3 | 3 | 2 | 3 | 2 | N |
| 13 | 50 | 2 | 2 | 5 | 3 | 3 | 2 | N |
| 14 | 50 | 4 | 4 | 5 | 2 | 5 | 5 | L |
| 15 | 50 | 4 | 3 | 5 | 4 | 5 | 5 | L |
| 16 | 50 | 4 | 4 | 5 | 2 | 5 | 5 | L |
| 17 | 50 | 3 | 2 | 4 | 3 | 3 | 5 | L |
| 19 | 50 | 5 | 3 | 3 | 2 | 4 | 4 | N |
| 21 | 50 | 4 | 3 | 5 | 3 | 3 | 5 | N |
| 22 | 50 | 2 | 2 | 4 | 5 | 5 | 5 | N |
| 23 | 50 | 2 | 2 | 5 | 2 | 2 | 2 | N |
| 24 | 50 | 4 | 4 | 5 | 5 | 5 | 5 | L |
| 25 | 25 | 5 | 5 | 5 | 5 | 5 | 5 | L |
| 26 | 50 | 2 | 5 | 5 | 5 | 5 | 5 | L |
| 27 | 50 | 5 | 5 | 5 | 5 | 5 | 5 | L |
| 28 | 50 | 4 | 4 | 5 | 5 | 5 | 5 | L |
| 29 | 50 | 3 | 2 | 5 | 5 | 5 | 5 | N |
| 30 | 50 | 3 | 2 | 5 | 2 | 3 | 2 | N |
| 31 | 50 | 2 | 2 | 5 | 2 | 2 | 2 | N |
| 32 | 50 | 2 | 4 | 5 | 5 | 5 | 5 | N |
| 33 | 50 | 4 | 4 | 5 | 5 | 5 | 5 | L |
| 34 | 50 | 4 | 3 | 5 | 4 | 4 | 2 | L |
| 36 | 50 | 2 | 3 | 4 | 5 | 3 | 2 | L |
| 37 | 50 | 2 | 3 | 5 | 5 | 3 | 5 | N |
| 38 | 50 | 3 | 2 | 5 | 5 | 5 | 5 | N |
| 40 | 50 | 5 | 3 | 4 | 5 | 5 | 5 | L |
| 41 | 50 | 3 | 3 | 5 | 5 | 5 | 5 | L |
| 42 | 50 | 4 | 5 | 5 | 3 | 5 | 5 | L |

TABLE 5-continued

| Compound No. | Amount of active ingredient applied (g/are) | Effect of post-emergence treatment ||||||  Chemical injury Soybean |
|---|---|---|---|---|---|---|---|---|
| | | Oats | Large crabgrass | Redroot pigweed | Mugwort | Gishi-gishi | Umbrella sedge | |
| 43 | 50 | 4 | 3 | 5 | 4 | 5 | 5 | L |
| 44 | 50 | 3 | 2 | 4 | 3 | 5 | 5 | L |
| 46 | 50 | 4 | 4 | 5 | 4 | 5 | 5 | L |
| 47 | 50 | 3 | 3 | 3 | 2 | 4 | 5 | N |
| 49 | 50 | 2 | 2 | 5 | 5 | 5 | 5 | N |
| 50 | 50 | 5 | 4 | 5 | 5 | 5 | 2 | N |
| 51 | 50 | 5 | 2 | 5 | 5 | 5 | 5 | L |
| 52 | 50 | 5 | 2 | 5 | 4 | 5 | 5 | N |
| 53 | 50 | 4 | 2 | 5 | 4 | 5 | 5 | L |
| 54 | 50 | 4 | 2 | 5 | 5 | 5 | 5 | N |
| 55 | 50 | 4 | 2 | 5 | 5 | 5 | 5 | N |
| 56 | 50 | 5 | 2 | 5 | 4 | 5 | 5 | N |
| 57 | 50 | 2 | 2 | 5 | 4 | 3 | 5 | N |
| 58 | 50 | 2 | 2 | 5 | 2 | 2 | 2 | N |
| 62 | 50 | 4 | 3 | 5 | 4 | 4 | 5 | N |
| 63 | 50 | 5 | 2 | 5 | 5 | 4 | 5 | N |
| 64 | 50 | 5 | 3 | 5 | 4 | 4 | 5 | N |
| 65 | 50 | 4 | 2 | 5 | 5 | 4 | 5 | N |
| 67 | 50 | 2 | 2 | 5 | 2 | 5 | 4 | L |
| 68 | 50 | 2 | 2 | 5 | 2 | 5 | 4 | L |
| 69 | 50 | 2 | 4 | 5 | 2 | 5 | 5 | L |
| 70 | 50 | 3 | 2 | 5 | 3 | 5 | 5 | L |
| 72 | 50 | 5 | 4 | 5 | 2 | 5 | 5 | L |
| 73 | 50 | 2 | 2 | 5 | 2 | 5 | 5 | N |
| 74 | 50 | 2 | 2 | 5 | 2 | 2 | 5 | N |
| 75 | 50 | 2 | 2 | 5 | 2 | 5 | 2 | N |
| 76 | 50 | 4 | 5 | 5 | 5 | 5 | 5 | L |
| 77 | 50 | 5 | 5 | 5 | 5 | 5 | 5 | L |
| 78 | 50 | 3 | 3 | 5 | 3 | 3 | 5 | L |
| 79 | 50 | 5 | 5 | 5 | 5 | 5 | 5 | L |
| 80 | 50 | 5 | 5 | 5 | 5 | 5 | 5 | L |
| 81 | 50 | 4 | 5 | 5 | 5 | 5 | 5 | L |
| 82 | 50 | 5 | 5 | 5 | 5 | 5 | 5 | L |
| 83 | 50 | 5 | 4 | 4 | 4 | 4 | 4 | L |
| 84 | 50 | 4 | 3 | 3 | 2 | 4 | 5 | L |
| 85 | 50 | 4 | 4 | 3 | 2 | 4 | 5 | L |
| 86 | 50 | 3 | 3 | 2 | 2 | 4 | 5 | N |
| 87 | 50 | 3 | 3 | 2 | 2 | 2 | 5 | L |
| 88 | 50 | 4 | 4 | 5 | 5 | 4 | 5 | L |
| 89 | 50 | 4 | 4 | 4 | 2 | 3 | 5 | L |
| 90 | 50 | 5 | 4 | 5 | 4 | 5 | 5 | L |
| 91 | 50 | 5 | 4 | 5 | 5 | 5 | 5 | L |
| 92 | 50 | 4 | 4 | 5 | 3 | 5 | 5 | L |
| 93 | 50 | 5 | 4 | 5 | 5 | 5 | 5 | L |

EXAMPLE 1

A wettable powder composition obtained by uniformly mixing and grinding the following constituents:

| | |
|---|---|
| Compound No. 43 | 50 parts |
| Mixture of clay and white carbon (clay is the major constituent) | 45 parts |
| Polyoxyethylene nonylphenyl ether | 5 parts |

EXAMPLE 2

A granule composition obtained by uniformly mixing and grinding the following constituents, kneading the mixture with a suitable amount of water, and granulating the kneaded mixture:

| | |
|---|---|
| Compound No. 69 | 5 parts |
| Mixture of bentonite and clay | 90 parts |
| Calcium liguninsulfonate | 5 parts |

EXAMPLE 3

An emulsifiable concentrate obtained by uniformly mixing the following constituents:

| | |
|---|---|
| Compound No. 92 | 50 parts |
| Xylene | 40 parts |
| Mixture of polyoxyethylene nonylphenyl ether and calcium alkylbenzenesulfonate | 10 parts |

SYNTHETIC PROCESS EXAMPLE 1

Synthesis of ethoxymethylene urethane

In 40 ml toluene was dissolved 44.4 g (0.3 mol) of ethyl orthoformate, and while keeping the temperature at 110°–120° C., 18 g (0.2 ml) of urethane and 200 ml of a mixture of sulfuric acid with toluene were dropped thereto spending about 2 hours, during which produced ethanol was distilled out of the reaction vessel. After the dropping had been finished, toluene was removed by distillation. The intended product (9.5 g) was obtained by distillation of the residue; b.p. 72.4° C. (15 mmHg), yield 38.8%.

SYNTHETIC PROCESS EXAMPLE 2

Synthesis of 1-(ethylthio)isobutylidene urethane

In 150 ml of ethyl ether were dissolved 34.5 g (0.5 ml) of isobutyronitrile and 31 g (0.5 mol) of ethyl mercaptan, and 20.1 g (0.55 mol) of dry hydrogen chloride was passed thereinto at a temperature not exceeding 0° C.

The reaction mixture was left 5 days at a temperature not exceeding 0° C., and thereafter 300 ml of n-hexane was added thereto. Oily matter separated as lower layer was collected, and after addition of ice, it was alkalified by addition of potassium carbonate at a temperature not exceeding 0° C. The produced oil was extracted with diethyl ether, dried, and distilled to remove ether, whereby 41.7 g of an oily substance was obtained. It was dissolved in 300 ml of benzene, admixed with 27.2 g of pyridine and while cooling the mixture at a temperature not exceeding 0° C., 35 g of ethyl chlorocarbonate was dropped thereto. After 2 hours' reaction at a temperature not exceeding 5° C., insoluble matter was filtered off, and distilled to remove benzene. Then, 34.5 g of the intended product was obtained by reduced pressure distillation of the residue; b.p. 87°–90° C. (3 mmHg), yield 34.0%.

In a similar way, 1-(ethylthio)ethylidene urethane was obtained from acetonitrile, ethyl mercaptan, and ethyl chlorocarbonate; b.p. 80°–82° C. (3 mmHg), yield 40.0%.

SYNTHETIC PROCESS EXAMPLE 3

Synthesis of 1-(2,4-dichloro-5-isopropoxyphenyl)-3-methyl-$\Delta^2$-1,2,4-triazolin-5-one In 70 ml of xylene, 7.38 g (0.031 ml) of 2,4-dichloro-5-isopropoxyphenylhydrazine and 5.5 g (0.031 mol) of 1-(ethylthio)ethylidene urethane were heated for 30 minutes at 80°–90° C., then cooled to room temperature, admixed with 3.17 g (0.031 mol) of triethylamine, and refluxed for 2 hours.

Extraction with 50 ml of 10% aqueous caustic soda solution was made 3 times, and the aqueous layer collected was washed with diethyl ether and acidified with hydrochloric acid. The resulting crystals were filtered off, washed with water, dried, and recrystallized from methanol, whereby 8.8 g of the intended product was obtained; m.p. 165.7° C., yield 92.6%.

SYNTHETIC PROCESS EXAMPLE 4

Synthesis of 1-(2,4-dichloro-5-isopropoxyphenyl)-3-methyl-4-allyl-$\Delta^2$-1,2,4-triazolin-5-one In 300 ml of benzene were suspended 9 g (0.03 mol) of 1-(2,4-dichloro-5-isopropoxyphenyl)-3-methyl-$\Delta^2$-1,2,4-triazolin-5-one and 9 g of triethylbenzylammonium chloride, and 40 ml of aqueous solution containing 9 g of caustic soda was added thereto. After 30 minutes' stirring, 4 g (0.033 mol) of allyl bromide was added thereto, and after 2 hours' reflux with stirring, the benzene layer was collected, washed successively with water, with dilute hydrochloric acid, and with water, dried, distilled to remove benzene, and further purified by dry column chromatography, whereby 9.4 g of the intended product was obtained; $n_D^{25}$ 1.5573, yield 91.4%.

SYNTHETIC PROCESS EXAMPLE 5

Synthesis of 1-(2,4-dichloro-5-isopropoxyphenyl)-3-t-butyl-4-methyl-$\Delta^2$-1,2,4-triazolin-5-one In 30 ml of tetrahydrofuran were dissolved 2.35 g (0.01 mol) of 2,4-dichloro-5-isopropoxyphenylhydrazine and 1.1 g (0.011 mol) of triethylamine, and 1.2 g (0.01 mol) of pivaloyl chloride was dropped thereto at a temperature not exceeding 10° C. After 30 minutes' stirring the formed salt was filtered off, and the filtrate was concentrated to obtain crystals. The crystals were dissolved in 50 ml of tetrahydrofuran, and 1 g of methyl isocyanate and two or three drops of triethylamine were added thereto. The mixture was refluxed for 40 hours, and to the oily matter obtained by distilling tetrahydrofuran off, 70 ml of 5% aqueous caustic potash was added. The mixture was refuxed for 30 minutes, then cooled to room temperature, and subjected to extraction with diethyl ether. The extract was dried, freed of ether by distillation, and further purified by dry column chromatography, whereby 0.34 g of the intended product was obtained; m.p. 112.5° C., yield 9.5%.

SYNTHETIC PROCESS EXAMPLE 6

Synthesis of 1-(2,4-dichloro-5-hydroxyphenyl)-3-methyl-4-allyl-$\Delta^2$-1,2,4-triazolin-5-one The mixture of 3.0 g (0.0087 mol) of 1-(2,4-dichloro-5-isopropoxyphenyl)-3-methyl-4-allyl-$\Delta^2$-1,2,4-triazolin-5one, 10 ml of 47% hydrobromic acid, and 50 ml of acetic acid was refluxed for 5 hours. Water (200 ml) was poured thereinto, and extraction with 50 ml of ethyl acetate was made 3 times. The ethyl acetate layer was twice subjected to extraction with 50 ml of 10% aqueous caustic soda. The water layer was acidified with hydrochloric acid, and the product was extracted with ethyl acetate. The extract was washed with water, dried, and freed or ethyl acetate by distillation, whereby 2.6 g of the intended product was obtained; m.p. 138.8° C., yield 100%.

SYNTHETIC PROCESS EXAMPLE 7

Synthesis of 1-(2,4-dichloro-5-sec-butoxyphenyl)-3-methyl-4-allyl-$\Delta^2$-1,2,4-triazolin-5-one In 20 ml of benzene were suspended 0.6 g (0.001 mol) of 1-(2,4-dichloro-5-hydroxyphenyl)-3-methyl-4-allyl-$\Delta^2$-1,2,4-triazolin-5-one and 0.6 g of triethylbenzylammonium chloride, and 2 ml of aqueous solution containing 0.6 g of caustic soda was added thereto. After 30 minutes' stirring at room temperature, 1 g of sec-butyl bromide was added, and the mixture was refluxed with stirring for 3 hours. After completion of the reaction, 50 ml of water was added, and the benzene layer was drawn, washed successively with water, with dilute hydrochloric acid, and again with water, then dried, freed or benzene by distillation, and purified by dry column chromatography, whereby 0.5 g of the intended product was obtained; $n_D^{24}$ 1.5552, yield 71.4%.

SYNTHETIC PROCESS EXAMPLE 8

Synthesis of
1-[2,4-dichloro-5-(1-ethoxycarbonylethoxy)phenyl]-3-methyl-4-allyl-Δ²-1,2,4-triazolin-5-one The mixture of 0.5 g (0.00166 mol) of 1-(2,4-dichloro-5-hydroxyphenyl)-3-methyl-4-allyl-Δ²-1,2,4-triazolin-5one, 0.31 g (0.0017 mol) of ethyl 2-bromopropionate, and 1 g of potassium carbonate was heated in 10 ml of dimethylsulfoxide at 100°–110° C. for 3 hours. After completion of the reaction, 50 ml of water was added, and the product was extracted with diethyl ether. The ether extract was washed, dried, freed of ether by distillation, and purified by dry column chromatography, whereby 0.4 g of the intended product was obtained; $n_D^{22}$ 1.5459, yield 60.6%.

SYNTHETIC PROCESS EXAMPLE 9

Synthesis of
1-(2,4-dichloro-5-ethoxymethoxyphenyl)-3-methyl-4-allyl-Δ²-1,2,4-triazolin-5-one In 50 ml of benzene were dissolved 3.0 (0.0087 mol) of 1-(2,4-dichloro-5-hydroxyphenyl)-3-methyl-4-allyl-Δ²-1,2,4-triazolin-5-one and 2.2 g of triethylamine, and 0.94 g (0.0098 mol) of chloromethyl ethyl ether was dropped thereto at a temperature not exceeding 10° C. After 1 hour's stirring at room temperature, water was added, and the benzene layer was drawn, dried, freed of benzene by distillation, whereby 3.1 g of the intended product was obtained; $n_D^{21}$ 1.5596, yield 86.4%.

SYNTHETIC PROCESS EXAMPLE 10

Synthesis of
1-[2,4-dichloro-5-(2-ethoxyethoxy)-phenyl]-3-methyl-4-allyl-Δ²-1,2,4-triazolin-5-one The mixture of 0.5 g (0.0015 mol) of 1-(2,4-dichloro-5-hydroxyphenyl)-3-methyl-4-allyl-Δ²-1,2,4-triazolin-5-one, 1 g of potassium fluoride, and 30 ml of dimethylformamide was stirred at room temperature for 30 minutes, and 1 g (0.0091 mol) of 2-chloroethyl ethyl ether was added thereto. The mixture was heated with stirring at 120° C. for 4 hours, and then cooled to room temperature. Water was added thereto, and the resulting oily matter was subjected to extraction with diethyl ether. The extract was washed successively with alkali solution and with water, dried, and freed of ether by distillation. The remaining oily matter was purified through a dry column of silica gel using the mixed solvent of ethyl acetate and n-hexane (1:1). Thus, 0.43 g of the intended product was obtained; $n_D^{21}$ 1.5579, yield 70.5%.

What is claimed is:

1. A Δ²-1,2,4-triazolin-5-one derivative represented by the formula

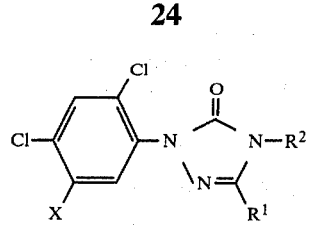

wherein $R^1$ is a $C_1$–$C_4$ alkyl; $R^2$ is a hydrogen atom, a $C_1$–$C_6$ alkyl group or a $C_2$–$C_4$ alkenyl group; and X is a hydroxy group, a $C_1$–$C_4$ alkyl group, a $C_1$–$C_6$ alkyloxy group, an alkyloxyalkyloxy group of which two alkyls may be same as or different from each other and each alkyl is of $C_1$–$C_4$, a $C_2$–$C_4$ alkenyloxy, or an alkyloxycarbonylalkyloxy group of which two alkyls may be same as or different from each other and each alkyl is of $C_1$–$C_4$.

2. A Δ²-1,2,4-triazolin-5-one derivative of claim 1, wherein $R^1$ is a $C_1$–$C_4$ alkyl group; $R^2$ is a $C_1$–$C_4$ alkyl group or allyl group; and X is a $C_1$–$C_4$ alkyloxy, methoxymethoxy, or allyloxy group.

3. 1-(2,4-dichloro-5-allyloxyphenyl)-3-isopropyl-4-methyl-Δ²-1,2,4-triazolin-5-one.

4. 1-(2,4-dichloro-5-isopropyloxyphenyl)-3-methyl-4-ethyl-Δ²-1,2,4-triazolin-5-one.

5. 1-(2,4-dichloro-5-isopropyloxyphenyl)-3-methyl-4-allyl-Δ²-1,2,4-triazolin-5-one.

6. 1-(2,4-dichloro-5-methoxymethoxyphenyl)-3-methyl-4-allyl-Δ²-1,2,4-triazolin-5-one.

7. A herbicidal composition comprising an herbicidally effective amount of a Δ²-1,2,4-triazolin-5-one derivative and a diluent, said derivative being represented by the formula

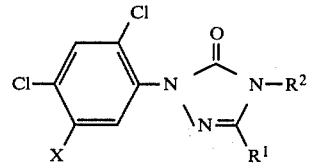

wherein, $R^1$ is a $C_1$–$C_4$ alkyl; $R^2$ is a hydrogen atom, a $C_1$–$C_6$ alkyl group, or a $C_2$–$C_4$ alkenyl group; and X is a hydroxy group, a $C_1$–$C_4$ alkyl group, a $C_1$–$C_6$ alkyloxy group, an alkyloxyalkyloxy group of which two alkyls may be same as or different from each other and each alkyl is of $C_1$–$C_4$, a $C_2$–$C_4$ alkenyloxy, or an alkyloxycarbonylalkyloxy group of which two alkyls may be same as or different from each other and each alkyl is of $C_1$–$C_4$.

8. A herbicidal composition of claim 7, wherein $R^1$ is a $C_1$–$C_4$ alkyl; $R^2$ is a $C_1$–$C_4$ alkyl or allyl; and X is a $C_1$–$C_4$ alkyloxy, methoxymethoxy, or allyloxy group.

9. A herbicidal composition according to claim 7, wherein said active ingredient is 1-(2,4-dichloro-5-allyloxyphenyl)-3-isopropyl-4-methyl-Δ²-1,2,4-triazolin-5-one.

10. A herbicidal composition according to claim 7, wherein said active ingredient is 1-(2,4-dichloro-5-isopropyloxyphenyl)-3-methyl-4-ethyl-Δ²-1,2,4-triazolin-5-one.

11. A herbicidal composition according to claim 7, wherein said active ingredient is 1-(2,4-dichloro-5-isopropyloxyphenyl)-3-methyl-4-allyl-Δ²-1,2,4-triazolin-5-one.

12. A herbicidal composition according to claim 7, wherein said active ingredient is 1-(2,4-dichloro-5-methoxymethoxyphenyl)-3-methyl-4-allyl-Δ²-1,2,4-triazolin-5-one.

* * * * *